(12) United States Patent
Heida et al.

(10) Patent No.: US 10,125,063 B2
(45) Date of Patent: Nov. 13, 2018

(54) COLUMN WITH SEPARATIVE INSTALLATIONS FOR SEPARATING A MIXTURE OF HYDROCARBONS AND/OR HYDROCARBON DERIVATIVES BY MEANS OF AN EXTRACTIVE DISTILLATION USING A SELECTIVE SOLVENT

(71) Applicant: BASF SE, Ludwigshafen (DE)

(72) Inventors: Bernd Heida, Ellerstadt (DE); Julia Hofinger, Ludwigshafen (DE); Peter Renze, Mannheim (DE)

(73) Assignee: BASF SE, Ludwigshafen (DE)

( * ) Notice: Subject to any disclaimer, the term of this patent is extended or adjusted under 35 U.S.C. 154(b) by 117 days.

(21) Appl. No.: 15/323,802

(22) PCT Filed: Jul. 7, 2015

(86) PCT No.: PCT/EP2015/065423
§ 371 (c)(1),
(2) Date: Jan. 4, 2017

(87) PCT Pub. No.: WO2016/005359
PCT Pub. Date: Jan. 14, 2016

(65) Prior Publication Data
US 2017/0158583 A1    Jun. 8, 2017

(30) Foreign Application Priority Data

Jul. 8, 2014    (EP) .................................... 14176082

(51) Int. Cl.
*B01D 15/08*    (2006.01)
*B01D 15/10*    (2006.01)
(Continued)

(52) U.S. Cl.
CPC .................. *C07C 7/08* (2013.01); *B01D 3/32* (2013.01); *B01D 3/40* (2013.01); *B01F 5/0415* (2013.01);
(Continued)

(58) Field of Classification Search
CPC ........ B01D 15/08; B01D 15/10; B01D 15/14; B01D 15/18
(Continued)

(56) References Cited

U.S. PATENT DOCUMENTS

| 2,129,684 A | * | 9/1938 | Gordon | ................... C07C 51/46 |
| | | | | 252/364 |
| 2,610,141 A | | 9/1952 | Drout, Jr. | |

(Continued)

FOREIGN PATENT DOCUMENTS

| CN | 101 588 851 A | 11/2009 |
| DE | 10 2010 011 014 A1 | 9/2011 |

(Continued)

OTHER PUBLICATIONS

International Preliminary Report on Patentability and Written Opinion dated Jan. 19, 2017 in PCT/EP2015/065423 (submitting English translation only).

(Continued)

*Primary Examiner* — Thuan D Dang
(74) *Attorney, Agent, or Firm* — Oblon, McClelland, Maier & Neustadt, L.L.P.

(57) ABSTRACT

What is proposed is a column (K) comprising separatory internals (E) for separating a mixture of hydrocarbons and/or hydrocarbon derivatives (1) by extractive distillation with a selective solvent (2),
with supply of the selective solvent (2) in the upper region of the column and supply of the mixture of hydrocarbons (Continued)

Figure 1:
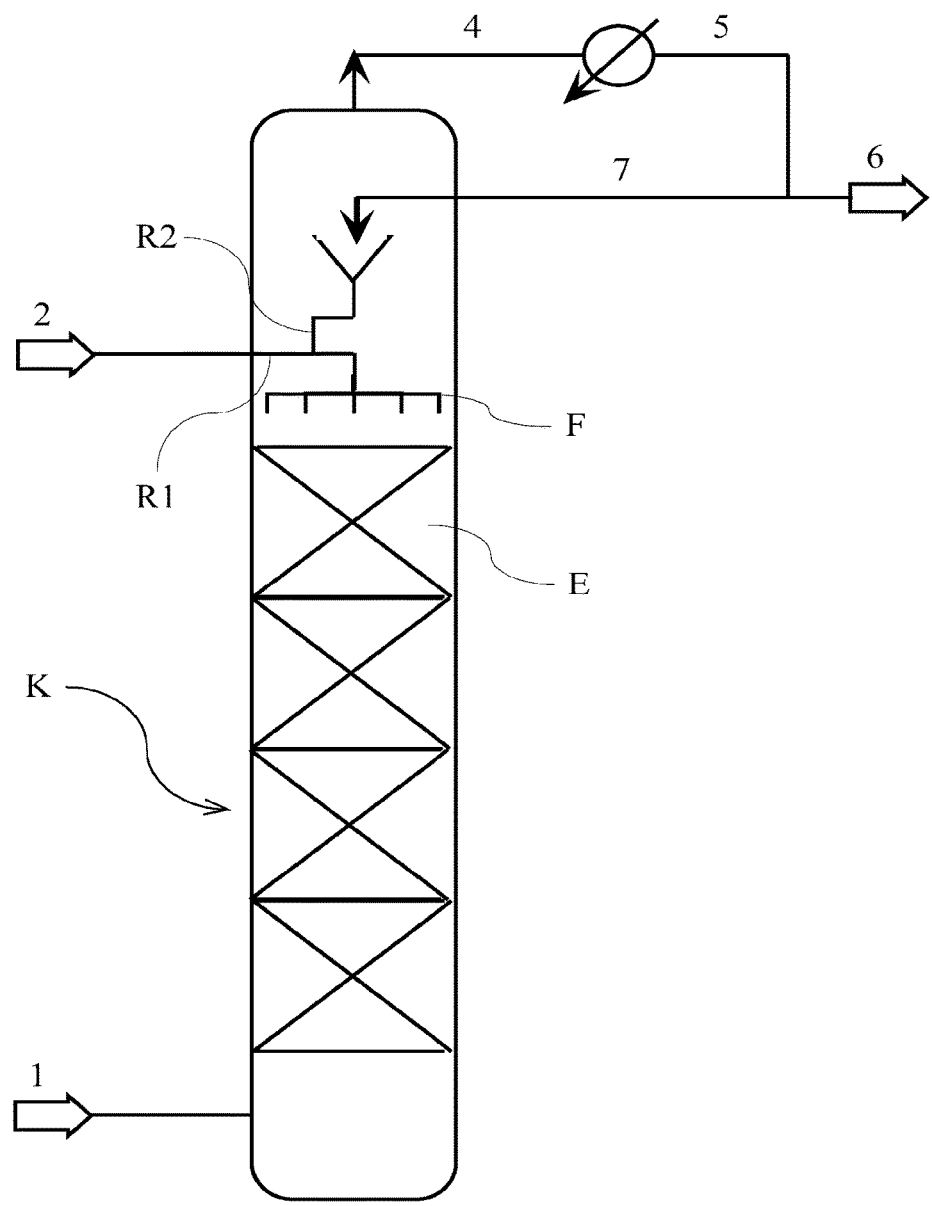

and/or hydrocarbon derivatives to be separated (1) below the supply of the selective solvent (2), the selective solvent (2) becoming laden in the column (K) with the components from the mixture to be separated (1) for which it has greater affinity and being withdrawn from the lower region of the column as laden selective solvent (3), while, by contrast, the components from the mixture to be separated for which the selective solvent (2) has a lower affinity remain in the vapor phase and are withdrawn as top stream (4), which is completely or partially condensed to obtain a condensate (5), some of which is withdrawn as product stream (6), the remainder being reintroduced to the column (K) as reflux (7), wherein said column comprises in the region of the column above the separatory internals (E) a first, substantially horizontal feed pipe (R1) for supplying the selective solvent, wherein the first, substantially horizontal feed pipe (R1) exhibits a cross-sectional narrowing to a narrowest point (V), said pipe widening again downstream of the cross-sectional narrowing, and wherein said column comprises a second feed pipe (R2) for supplying the reflux (7), said pipe joining the first, substantially horizontal feed pipe (R1) in the region of the narrowest point (V) of the cross-sectional narrowing.

14 Claims, 2 Drawing Sheets

(51) Int. Cl.
*B01D 15/14* (2006.01)
*B01D 15/18* (2006.01)
*C07C 7/10* (2006.01)
*C07C 7/08* (2006.01)
*B01D 3/32* (2006.01)
*B01D 3/40* (2006.01)
*B01F 5/04* (2006.01)
*B01F 5/06* (2006.01)
*C10G 21/20* (2006.01)

(52) U.S. Cl.
CPC ............ *B01F 5/0428* (2013.01); *B01F 5/061* (2013.01); *C10G 21/20* (2013.01); *B01F 2005/0636* (2013.01)

(58) Field of Classification Search
USPC .................. 202/152, 158; 585/833, 834, 862
See application file for complete search history.

(56) References Cited

U.S. PATENT DOCUMENTS

| | | |
|---|---|---|
| 2,663,679 A | 12/1953 | Drout, Jr. |
| 4,802,630 A | 2/1989 | Kromrey et al. |
| 9,273,829 B2 | 3/2016 | Weickert et al. |
| 2005/0059838 A1 | 3/2005 | Yada et al. |

FOREIGN PATENT DOCUMENTS

| | | |
|---|---|---|
| FR | 2 606 291 A1 | 5/1988 |
| WO | 99/03554 A1 | 1/1999 |

OTHER PUBLICATIONS

U.S. Appl. No. 14/915,035, filed Feb. 26, 2016, US 2016-0207852 A1, Matthias Kern et al.
U.S. Appl. No. 14/912,809, filed Feb. 18, 2016, US 2016-0207767 A1, Matthias Kern et al.
U.S. Appl. No. 14/911,747, filed Feb. 12, 2016, US 2016-0186932 A1, Matthias Weickert et al.
U.S. Appl. No. 14/911,756, filed Feb. 12, 2016, US 2016-0201853 A1, Matthias Weickert et al.
U.S. Appl. No. 14/911,789, filed Feb. 12, 2016, US 2016-0201854 A1, Matthias Weickert et al.
International Search Report dated Sep. 28, 2015 in PCT/EP2015/065423 filed Jul. 7, 2015.

\* cited by examiner

COLUMN WITH SEPARATIVE INSTALLATIONS FOR SEPARATING A MIXTURE OF HYDROCARBONS AND/OR HYDROCARBON DERIVATIVES BY MEANS OF AN EXTRACTIVE DISTILLATION USING A SELECTIVE SOLVENT

The invention relates to a column comprising separatory internals for separating a mixture of hydrocarbons and/or hydrocarbon derivatives by extractive distillation with a selective solvent and to a process employing the column.

Extractive distillation columns are used for separating mixtures of hydrocarbons and/or hydrocarbon derivatives using a selective solvent which increases the volatility differences between the components of the mixture to be separated. The mixture to be separated and the selective solvent are passed over the separatory internals of the column in countercurrent, the selective solvent becoming laden with the components from the mixture to be separated for which it has greater affinity and being withdrawn from the lower region of the column as laden selective solvent while, by contrast, the components from the mixture to be separated for which the selective solvent has a lower affinity remain in the vapor phase and are withdrawn as top stream which is completely or partially condensed to obtain a condensate, some of which is withdrawn as product stream, the remainder being reintroduced to the column as reflux.

Efficient operation of the column requires that the reflux is uniformly mixed with the selective solvent and dissolved therein to obtain a monophasic liquid solution of homogeneous composition.

In the case of prior art columns which lack the inventive premixing of selective solvent and reflux, i.e. with separate supply thereof, the column suffers a considerable loss of efficiency because the dissolution and homogenization of the two liquids is at least partially effected in the upper region of the separatory internals and said internals are thus not available for the actual separation task. Thus, a column of 4.70 m in diameter suffers an efficiency loss in the range of up to 60% in the extractive distillation for removing 1,3-butadiene from a $C_4$ cut with N-methylpyrrolidone as selective solvent.

An example of a solution that has been proposed for the above problem is the disposal of two liquid distributors above one another and the introduction of one of the liquid streams to be mixed onto each of said distributors. This may achieve a partial improvement in the efficiency of the column but at the expense of additional installed height.

It is accordingly an object of the invention to provide an extractive distillation column which ensures exceptional mixing of reflux and selective solvent without this being at the expense of efficiency losses or additional installed height of the column.

The object is achieved by a column comprising separatory internals for separating a mixture of hydrocarbons and/or hydrocarbon derivatives by extractive distillation with a selective solvent, with supply of the selective solvent in the upper region of the column and supply of the mixture of hydrocarbons and/or hydrocarbon derivatives to be separated below the supply of the selective solvent, the selective solvent becoming laden in the column with the components from the mixture to be separated for which it has greater affinity and being withdrawn from the lower region of the column as laden selective solvent while, by contrast, the components from the mixture to be separated for which the selective solvent has a lower affinity remain in the vapor phase and are withdrawn as top stream which is completely or partially condensed to obtain a condensate, some of which is withdrawn as product stream, the remainder being reintroduced to the column as reflux, wherein
said column comprises in the region of the column above the separatory internals a first, substantially horizontal feed pipe for supplying the selective solvent,
wherein the first, substantially horizontal feed pipe exhibits a cross-sectional narrowing to a narrowest point, said pipe widening again downstream of the cross-sectional narrowing, and wherein
said column comprises a second feed pipe for supplying the reflux, said pipe joining the first, substantially horizontal feed pipe in the region of the narrowest point of the cross-sectional narrowing.

Those skilled in the art of extractive distillations would not have employed an admixing apparatus for admixing the reflux into the selective solvent in the above form which utilizes the Venturi effect, in particular because of the concern that the motive jet, which in the present case is the selective solvent stream, could aspirate gas to form gas bubbles which have a negative effect on the uniform distribution of the liquid over the column cross section.

However, it has been found that, surprisingly, in the region of the narrowest point of the cross-sectional narrowing in the first, substantially horizontal feed pipe a dynamic equilibrium is established which may essentially be described as follows:

The suction effect of the liquid jet of the selective solvent which flows in through the first, substantially horizontal feed pipe ceases as soon as a certain amount of gas is aspirated via the second feed pipe which joins the first, substantially horizontal feed pipe in the region of the narrowest point of the cross-sectional narrowing; a column of liquid backs up in the second feed pipe, said column being eliminated again very rapidly however, since the suction effect is established again as soon as even a small column of liquid has built up in the second feed pipe. The gas that has already been aspirated is completely dissolved in the liquid due to the high turbulences downstream of the narrowest point of the cross-sectional narrowing.

Any prior art extractive distillation column may be employed in accordance with the invention. Preference is given to columns on a world scale because for large column diameters, in particular larger than 0.5 m or else larger than 1.5 m, dissolution and homogenization of the reflux with the selective solvent becomes more difficult with increasing column diameter. The separatory internals may in particular be trays or packings. In the case of packings, liquid distributors disposed thereabove are always necessary.

It is advantageous when there is a liquid distributor disposed above the separatory internals in the column.

In the case of trays as separatory internals an additional liquid distributor disposed above said trays is not strictly necessary; it is also possible for the uppermost trays to assume the function of said liquid distributor though these are then no longer available for the actual separation task.

The liquid distributor distributes the liquid uniformly over the column cross section and comprises fittings of a type such that the steam is passed upward through the column separately from the liquid. Examples of liquid distributors that may be used include trough distributors, perforated plate distributors, nozzle distributors or pipe distributors.

The reflux is preferably introduced onto separatory internals, in particular trays, to scrub out the solvent from the ascending vapor.

Mixing the two liquid streams is all the more difficult the greater the differences in density and viscosity. This applies in particular for density differences greater than about 3% to 5% and viscosity differences greater than about 50%.

Problems are encountered, for example, in the mixing of so-called raffinate 1, i.e. a mixture essentially comprising butanes and butenes, with N-methylpyrrolidone and 8.3 wt % of water as selective solvent since both liquids differ markedly in terms of density (NMP/water=1.014 kg/m$^3$ versus raffinate 1=572 kg/m$^3$) and viscosity (NMP/water=1.179 mPa·s versus raffinate 1=0.14 mPa·s).

The particular configuration of the first, substantially horizontal feed pipe comprising a cross-sectional narrowing to a narrowest point and an adjoining widening utilizes the well-known Venturi effect, i.e. the constriction generates locally elevated velocities which causes the second liquid stream to be aspirated via the second feed pipe disposed in the region of the narrowest point of the cross-sectional narrowing, i.e. of the constriction, without the need for a feed pump or static pressure. Exploiting the Venturi effect thus makes it possible to achieve thorough commixing for liquid streams without the use of moving parts and without the additional installed height that would be necessary for application of static pressure.

Herein, the first feed pipe is to be disposed substantially horizontally in the column, which is to be understood as meaning that small deviations from the horizontal due to fabrication- and installation-dependent factors of up to 5 degrees or else of up to 10 degrees are also encompassed.

It is advantageous when the ratio of the cross section of the first, substantially horizontal feed pipe upstream of the cross-sectional narrowing to the cross section of the first, horizontal feed pipe at the narrowest point of the cross-sectional narrowing is chosen such that the pressure inside the first, substantially horizontal feed pipe at the narrowest point of the cross-sectional narrowing is higher than the pressure outside the first, substantially horizontal feed pipe immediately proximal to the narrowest point of the cross-sectional narrowing.

It is further preferable for the diameter of the first, substantially horizontal feed pipe upstream of the cross-sectional narrowing to be chosen such that the flow velocity in the first, substantially horizontal feed pipe upstream of the cross-sectional narrowing is in the range of from 0.1 to 5.0 m/s, preferably in the range of from 0.3 to 1.5 m/s.

The geometry of the first, substantially horizontal feed pipe is preferably chosen such that the cross-sectional narrowing spans a length of up to 4 times the diameter of the first, substantially horizontal feed pipe, preferably of up to 3 times, and the widening downstream of the narrowest point of the cross-sectional narrowing spans a length of between 0.1 times the diameter of the first, substantially horizontal feed pipe and 15 times the diameter of the first, substantially horizontal feed pipe.

This particular configuration of the first, substantially horizontal feed pipe seeks to achieve a minimized length of said pipe, in order that the installation costs thereof are as low as possible.

In one advantageous configuration the second feed pipe that joins the first, substantially horizontal feed pipe in the region of the narrowest point of the cross-sectional narrowing preferably protrudes into said pipe by a protrusion depth of from 0.1 to 0.8 times the diameter of the second feed pipe, preferably by a protrusion depth of from 0.15 to 0.75 times the diameter of the second feed pipe.

This preferred configuration of the second feed pipe achieves an additional improvement in mixing over the cross section of the first, substantially horizontal pipe. It is further preferred when the second feed pipe protruding into the first, substantially horizontal pipe terminates slantedly at an angle to the longitudinal axis of said second feed pipe in the range of from 4° to 65°.

This further preferred configuration achieves a further improvement in mixing over the cross section of the first, substantially horizontal feed pipe due to amplified separation vortices at the end of the second feed pipe and an altogether stronger aspiratory effect.

In a further improved embodiment the first, substantially horizontal feed pipe has disposed in it, downstream of the narrowest point of the cross-sectional narrowing and substantially transversely to the longitudinal axis of said pipe, a substantially planar static mixing element that partially blocks the cross section of said pipe.

The static mixing element provided in the present case shall be substantially planar, i.e. its dimension in the longitudinal direction of the first, substantially horizontal feed pipe shall be negligible compared to its two other dimensions.

The substantially planar static mixing element shall partially block the cross section of the first, substantially horizontal feed pipe, preferably blocking in the range of from 5% to 50% thereof.

The substantially planar static mixing element is preferably spaced apart from the point of the narrowest cross section of the first, substantially horizontal feed pipe by at least double the diameter of said pipe at the point of the narrowest cross section of said pipe.

It is advantageous when the static mixing element is eccentrically disposed in the cross section of the first, substantially horizontal feed pipe and is in contact with the interior wall of said pipe or is close to the wall thereof but in the upper region of the first, substantially horizontal feed pipe is spaced apart from the interior wall of said pipe.

It is preferred when the static mixing element eccentrically disposed in the first, substantially horizontal feed pipe is in the shape of an annulus.

In a further preferred embodiment the static mixing element eccentrically disposed in the first, substantially horizontal feed pipe is in the shape of an annulus which is open at the top, said annulus preferably being secured to the interior wall by means of supports in the upper region of said interior wall.

The invention also provides a process for separating a mixture of hydrocarbons and/or hydrocarbon derivatives by extractive distillation with a selective solvent in a column with supply of the selective solvent in the upper region of the column and supply of the mixture of hydrocarbons and/or hydrocarbon derivatives to be separated below the supply of the selective solvent, the selective solvent becoming laden in the column with the components from the mixture to be separated for which it has greater affinity and being withdrawn from the lower region of the column as laden selective solvent while, by contrast, the components from the mixture of hydrocarbons and/or hydrocarbon derivatives to be separated for which the selective solvent has a lower affinity remain in the vapor phase and are withdrawn as top stream which is completely or partially condensed to obtain a condensate, some of which is withdrawn as product stream, the remainder being reintroduced into the column as reflux, wherein the selective solvent is supplied into the upper region of the column above the separatory internals via a first, substantially horizontal feed pipe, wherein the first, substantially horizontal feed pipe exhibits a cross-sectional narrowing to a narrowest point, said pipe widening again downstream of the cross-sectional narrowing, and wherein the reflux is supplied via a second feed pipe which joins the first, substantially horizontal feed pipe at the narrowest point of the cross-sectional narrowing.

The process according to the invention is preferably an extractive distillation of C4 cuts to obtain butanes and/or butenes and/or 1,3-butadiene with a selective solvent selected from N-methylpyrrolidone or mixtures thereof with water, dimethylformamide and acetonitrile or an extractive distillation of aromatics-containing mixtures to obtain benzene and/or toluene and/or xylene.

The invention is more particularly elucidated hereinbelow with the aid of a drawing and working examples.

Figure 2:
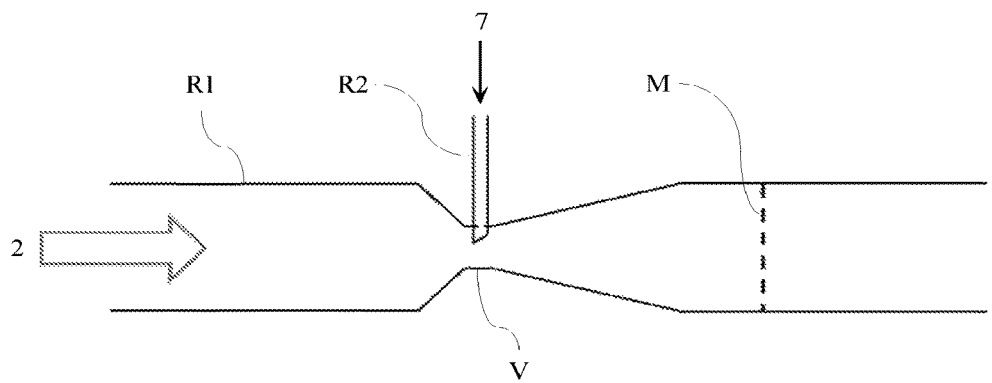
Figure 3A:
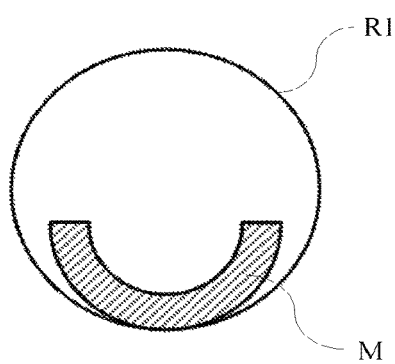
Figure 3B:
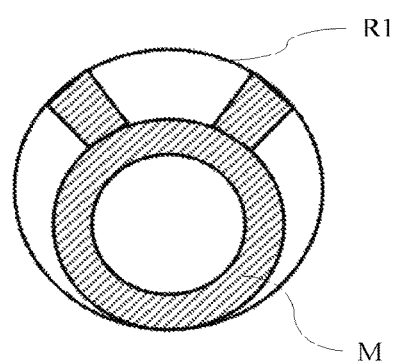

In the drawing, in particular,

FIG. 1 shows a schematic diagram of a preferred embodiment of a column according to the invention, FIG. 2 shows a schematic diagram of a preferred embodiment for a first feed pipe, said pipe being substantially horizontally disposed in the column, in the region of the narrowest point of the cross-sectional narrowing in the first, substantially horizontal feed pipe and with a static mixing element downstream of the narrowest point of the cross-sectional narrowing in the first, substantially horizontal feed pipe and FIGS. 3A and 3B show examples of preferred embodiments of static mixing elements FIG. 1 shows a preferred embodiment for an inventive column K for performing an extractive distillation of a mixture of hydrocarbons and/or hydrocarbon derivatives 1 by running said mixture in countercurrent to a selective solvent 2 over separatory internals E, with a liquid distributor F disposed above said internals, the selective solvent 2 becoming laden in the column K with the components from the mixture to be separated 1 for which it has greater affinity and being withdrawn from the lower region of the column as laden selective solvent 3 while, by contrast, the components from the mixture to be separated for which the selective solvent 2 has a lower affinity remain in the vapor phase and are withdrawn as top stream 4 which is condensed to obtain a condensate 5, some of which is withdrawn as product stream 6, the remainder being reintroduced to the column K as reflux 7.

The selective solvent 2 is fed into the column via a substantially horizontal feed pipe R1 above the internals E and the liquid distributor F. The substantially horizontal feed pipe R1 has a geometry that induces a Venturi effect, i.e. the feed pipe R1 has a cross-sectional narrowing to a narrowest point after which said pipe widens again, the reflux 7 being aspirated from a second feed pipe R2 in the region of the narrowest point of the cross-sectional narrowing, without the need for a feed pump or static pressure.

The schematic diagram in FIG. 2 elucidates the invention-essential admixing element for admixing the reflux 7 into the selective solvent 2: the selective solvent 2 is supplied via a first feed pipe R1 which exhibits a cross-sectional narrowing to a narrowest cross section V and subsequently widens again. In the region of the narrowest point V of the cross-sectional narrowing, the second feed pipe R2 is arranged through which the reflux 7 is passed and admixed into the stream 2 of the selective solvent. The preferred embodiment shown achieves an additional improvement in mixing quality when a static mixer M is disposed downstream of the narrowest point V of the cross-sectional narrowing and transversely to the main flow direction through the first feed pipe R1.

Preferred geometric configurations for static mixers M are shown in FIGS. 3A and 3B: in the shape of an annulus which is open at the top and is in contact with the lower interior wall of the pipe R1 in FIG. 3A, and in the shape of an eccentrically disposed annulus likewise in contact with the lower interior wall of the first feed pipe R1 but spaced apart from the upper interior wall of said pipe and secured thereto with supports in FIG. 3B.

WORKING EXAMPLES

Into an extractive distillation column K having an internal diameter of 5.33 m is fed, above the separatory internals E and at a mass flow rate of 417 t/h, a stream of selective solvent 2 comprising an N-methylpyrolidone/water mixture having a density of 1013.7 kg/m$^3$ and a viscosity of 1.179 mPa·s. The reflux 7 introduced at a mass flow rate of 22 t/h comprises a mixture of butanes and butenes having a density of 572.1 kg/m$^3$ and a viscosity of 0.14 mPa·s.

Comparative Example

For comparison, the extractive distillation column K has a commercially available perforated plate liquid distributor disposed in it above the separatory internals E. In the plane of the openings for issuance of liquid from the liquid distributor, mixing quality $X_{max}/X_{av}$, as defined hereinbelow, has a value of 6.8.

When reporting mixing quality, $X_{max}$ presently describes the highest value in the measurement zone for the mass fraction of stream 7.

Correspondingly, $X_{av}$ describes the average value in the measurement zone for the mass fraction of stream 7, i.e. the value to be found in the entire measurement zone in the case of perfect mixing.

Mixing quality is defined by the ratio $X_{max}/X_{av}$. Accordingly, mixing quality is 1 in the case of ideal mixing.

The ratio $X_{min}/X_{av}$ is defined analogously, i.e., as the ratio of the lowest value in the measurement zone to the average value in the measurement zone, in each case for the mass fraction of stream 7.

Inventive Examples

Example 1

Admixing apparatus provided above the separatory internals E is a first, substantially horizontally disposed feed pipe R1 exhibiting a cross-sectional narrowing to a narrowest point V, said pipe widening again afterwards. In the region of the narrowest point V of the cross-sectional narrowing, a second feed pipe R2 joins therewith, partially protrudes into the first, substantially horizontal feed pipe R1 and has a slanted end.

The specific measurements are as follows:

diameter of the first, substantially horizontal feed pipe R1=304.8 mm, cross-sectional narrowing of the first, substantially horizontal feed pipe R1 extends over a length of 150 mm in the longitudinal direction of said pipe, region of the narrowest point V of the cross-sectional narrowing: extends over 75 mm in the longitudinal direction of the first, substantially horizontal feed pipe R1, diameter at the narrowest point V of the first, substantially horizontal feed pipe R1=130 mm, an adjacent widening to the original diameter of 304.8 mm extending over a length of 480 mm of the first, substantially horizontal feed pipe R1.

In the region of the narrowest point V of the cross-sectional narrowing, a second feed pipe R2 having an internal diameter of 50.8 mm protrudes into the first, substantially horizontal feed pipe R1 to a protrusion depth of 49.2 mm at the upstream end and to a protrusion depth of 29.2 mm at the downstream end, i.e. the second feed pipe R2 is slanted.

The mixing quality values which follow are determined in a measurement zone defined as a cross section of the first, substantially horizontal feed pipe R1 at a distance of 2 m downstream of the downstream-facing end of the narrowest point V of the cross-sectional narrowing:

$X_{max}/X_{av}$ equals 1.09 and $X_{min}/X_{av}$ equals 0.85.

Example 2

The setup in Example 2 is the same as the setup in Example 1 except that, in addition, disposed downstream of the feed pipes R1 and R2, there is a static mixing element M corresponding to the schematic diagram in FIG. 3B, which is in the shape of an eccentrically disposed ring and is made of a steel sheet and is of 4 mm in thickness, 260 mm in external diameter and 200 mm in internal diameter, said ring being in contact with the lower interior wall of the first, substantially horizontal feed pipe R1 and being secured to the upper interior wall of said pipe with two supports.

The mixing quality determined in this case is 1.02 for $X_{max}/X_{av}$ and 0.99 for $X_{min}/X_{av}$.

LIST OF REFERENCE NUMERALS

Streams:
1 mixture of hydrocarbons and/or hydrocarbon derivatives
2 selective solvent
3 laden, selective solvent
4 top stream
5 condensate
6 product stream
7 reflux
Apparatuses and Apparatus Parts:
K column
E separatory internals
F liquid distributor
R1 first, substantially horizontal feed pipe
R2 second feed pipe
V narrowest point of cross-sectional narrowing

The invention claimed is:

1. A column (K), comprising separatory internals (E) for separating a mixture of hydrocarbons and/or hydrocarbon derivatives (1) by extractive distillation with a selective solvent (2),
  with supply of the selective solvent (2) in the upper region of the column and supply of the mixture of hydrocarbons and/or hydrocarbon derivatives to be separated (1) below the supply of the selective solvent (2), the selective solvent (2) becoming laden in the column (K) with the components from the mixture to be separated (1) for which it has greater affinity and being withdrawn from the lower region of the column as laden selective solvent (3),
  while, by contrast, the components from the mixture to be separated for which the selective solvent (2) has a lower affinity remain in the vapor phase and are withdrawn as top stream (4),
  which is completely or partially condensed to obtain a condensate (5),
  some of which is withdrawn as product stream (6), the remainder being reintroduced to the column (K) as reflux (7),
  wherein
    said column comprises in the region of the column above the separatory internals (E) a first, substantially horizontal feed pipe (R1) for supplying the selective solvent,
    wherein the first, substantially horizontal feed pipe (R1) exhibits a cross-sectional narrowing to a narrowest point (V), said pipe widening again downstream of the cross-sectional narrowing, and wherein
    said column comprises a second feed pipe (R2) for supplying the reflux (7), said pipe joining the first, substantially horizontal feed pipe (R1) in the region of the narrowest point (V) of the cross-sectional narrowing.

2. The column (K) according to claim 1, wherein there is a liquid distributor (F) disposed above the separatory internals (E) in the column (K).

3. The column (K) according to claim 1, wherein said column has a diameter of >0.5 m.

4. The column (K) according to claim 1, wherein the ratio of the cross section of the first, substantially horizontal feed pipe (R1) upstream of the cross-sectional narrowing to the cross section of the first, horizontal feed pipe (R1) at the narrowest point (V) of the cross-sectional narrowing is chosen such that the pressure inside the first, substantially horizontal feed pipe (R1) at the narrowest point (V) of the cross-sectional narrowing is lower than the pressure outside the first, substantially horizontal feed pipe (R1) immediately proximal to the narrowest point (V) of the cross-sectional narrowing.

5. The column (K) according to claim 1, wherein the diameter of the first, substantially horizontal feed pipe (R1) upstream of the cross-sectional narrowing is chosen such that the flow velocity in the first, substantially horizontal feed pipe (R1) upstream of the cross-sectional narrowing is in the range of from 0.1 to 5.0 m/s.

6. The column (K) according to claim 1, wherein the second feed pipe (R2) that joins the first, substantially horizontal feed pipe (R1) in the region of the narrowest point (V) of the cross-sectional narrowing preferably protrudes into said pipe by a protrusion depth of from 0.1 to 0.8 times the diameter of the second feed pipe (R2).

7. The column (K) according to claim 6, wherein the second feed pipe protruding into the first, substantially horizontal pipe terminates slantedly at an angle to the longitudinal axis of said second feed pipe in the range of from 4° to 65°.

8. The column (K) according to claim 1, wherein the first, substantially horizontal feed pipe has disposed in it, downstream of the narrowest point of the cross-sectional narrowing and substantially transversely to the longitudinal axis of said pipe, a static mixing element (M) that partially blocks the cross section of said pipe.

9. The column (K) according to claim 8, wherein the static mixing element (M) is spaced apart from the point of the narrowest cross section (V) in the first, substantially horizontal feed pipe (R1) by at least double the diameter of the first, substantially horizontal feed pipe (R1) at the point of the narrowest cross section (V).

10. The column (K) according to claim 8, wherein the static mixing element (M) is eccentrically disposed in the cross section of the first, substantially horizontal feed pipe (R1) and is in contact with the interior wall of said pipe or is close to the wall thereof but in the upper region of the first, substantially horizontal feed pipe (R1) is spaced apart from the interior wall of said pipe.

11. The column (K) according to claim 10, wherein the static mixing element (M) eccentrically disposed in the first, substantially horizontal feed pipe (R1) is in the shape of an annulus.

12. The column (K) according to claim 11, wherein the static mixing element (M) eccentrically disposed in the first, substantially horizontal feed pipe (R1) is in the shape of an annulus which is open at the top, said annulus preferably being secured to the interior wall by means of supports in the upper region of said interior wall.

13. A process for separating a mixture of hydrocarbons and/or hydrocarbon derivatives (1) by extractive distillation with a selective solvent (2) in a column (K) according to claim 1, with supply of the selective solvent (2) in the upper region of the column and supply of the mixture of hydrocarbons and/or hydrocarbon derivatives to be separated (1) below the supply of the selective solvent (2), the selective solvent (2) becoming laden in the column (K) with the components from the mixture to be separated for which it has greater affinity and being withdrawn from the lower region of the column as laden selective solvent (3), while, by contrast, the components from the mixture of hydrocarbons and/or hydrocarbon derivatives (1) to be separated for which the selective solvent (2) has a lower affinity remain in the vapor phase and are withdrawn as top stream (4), which is completely or partially condensed to obtain a condensate (5), some of which is withdrawn as product stream (6), the remainder being reintroduced to the column as reflux (7), wherein the selective solvent (2) is supplied into the upper region of the column above the separatory internals (E) via a first, substantially horizontal feed pipe (R1), wherein the first, substantially horizontal feed pipe (R1) exhibits a cross-sectional narrowing to a narrowest point (V), said pipe widening again downstream of the cross-sectional narrowing, and wherein the reflux (7) is supplied via a second feed pipe (R2) which joins the first, substantially horizontal feed pipe (R1) at the narrowest point (V) of the cross-sectional narrowing.

14. The process according to claim 13, wherein said process is an extractive distillation of $C_4$ cuts to obtain butanes and/or butenes and/or 1,3-butadiene with a selective solvent selected from N-methylpyrrolidone or mixtures thereof with water, dimethylformamide and acetonitrile or an extractive distillation of aromatics-containing mixtures to obtain benzene and/or toluene and/or xylene.

* * * * *